(12) United States Patent
Zack

(10) Patent No.: US 10,616,955 B1
(45) Date of Patent: Apr. 7, 2020

(54) PERSONAL SAUNA UNIT WITH INTEGRATED CHROMOTHERAPY LIGHTING

(71) Applicant: Sunlighten, Inc., Overland Park, KS (US)

(72) Inventor: Aaron Michael Zack, Overland Park, KS (US)

(73) Assignee: Sunlighten, Inc., Overland Park, KS (US)

(*) Notice: Subject to any disclaimer, the term of this patent is extended or adjusted under 35 U.S.C. 154(b) by 236 days.

(21) Appl. No.: 15/440,158

(22) Filed: Feb. 23, 2017

Related U.S. Application Data

(60) Provisional application No. 62/298,768, filed on Feb. 23, 2016.

(51) Int. Cl.
| | | |
|---|---|---|
| *H05B 3/00* | (2006.01) | |
| *A61N 5/06* | (2006.01) | |
| *A61H 33/06* | (2006.01) | |
| *A61H 33/00* | (2006.01) | |

(52) U.S. Cl.
CPC ......... *H05B 3/0085* (2013.01); *A61H 33/005* (2013.01); *A61H 33/06* (2013.01); *A61N 5/0618* (2013.01); *A61N 5/0625* (2013.01); *A61N 2005/066* (2013.01); *A61N 2005/0626* (2013.01); *A61N 2005/0639* (2013.01); *A61N 2005/0651* (2013.01); *A61N 2005/0663* (2013.01)

(58) Field of Classification Search
CPC .... A61H 33/06; H05B 3/0085; A61N 5/0614; A61N 2005/0615; A61N 2005/0639
USPC ......................................................... 607/81
See application file for complete search history.

(56) References Cited

U.S. PATENT DOCUMENTS

| | | | | |
|---|---|---|---|---|
| 3,902,488 A | | 9/1975 | Sheppard | |
| 4,044,772 A | | 8/1977 | Schloss | |
| 4,055,863 A | * | 11/1977 | Duval | A61G 7/0005 |
| | | | | 4/601 |
| 4,918,319 A | * | 4/1990 | Kruithof | A61N 5/0614 |
| | | | | 250/493.1 |

(Continued)

FOREIGN PATENT DOCUMENTS

| | | | | |
|---|---|---|---|---|
| WO | 2007117234 A1 | 10/2007 | | |
| WO | WO-2007112939 A2 | * 10/2007 | ........... | A61N 5/0614 |

*Primary Examiner* — Nathan J Jenness
*Assistant Examiner* — Zahed Kabir
(74) *Attorney, Agent, or Firm* — Erickson Kernell IP, LLC; Kent R. Erickson

(57) ABSTRACT

A personal sauna unit with an integrated chromotherapy unit. The sauna unit is configured for use by a single person lying generally prone on a surface. The sauna unit includes a cabin that is disposed to overlie the user and that includes a plurality of infrared heating elements that direct infrared energy toward the user's body. When using the sauna unit, the user's head extends from an open end of the cabin. A chromotherapy light unit is integrated with the cabin to extend along the perimeter of the open end of the cabin and to direct a selected spectrum of visible light toward the user's face for therapy. A pad with additional heating elements may be provided beneath the cabin to provide additional heating and comfort to the user. A control unit is provided to control the heating elements and the light element during a sauna session.

19 Claims, 6 Drawing Sheets

(56) References Cited

U.S. PATENT DOCUMENTS

| | | | |
|---|---|---|---|
| 5,136,735 A * | 8/1992 | Zimmerman | A61G 7/0005 |
| | | | 4/597 |
| 6,066,087 A * | 5/2000 | Tron | A61H 33/06 |
| | | | 600/21 |
| 6,255,786 B1 | 7/2001 | Yen | |
| 6,489,614 B1 | 12/2002 | Deguchi et al. | |
| 6,549,809 B2 | 4/2003 | Ono | |
| 6,613,071 B1 * | 9/2003 | Fujii | A61N 5/06 |
| | | | 607/91 |
| 6,615,419 B1 | 9/2003 | Chang | |
| 7,108,712 B2 | 9/2006 | Barghelame | |
| 7,135,035 B1 | 11/2006 | Dimmick | |
| 7,575,549 B2 | 8/2009 | Miller | |
| 8,084,715 B2 | 12/2011 | Hall | |
| 8,602,398 B2 | 12/2013 | Hayasi et al. | |
| 8,692,168 B2 * | 4/2014 | Benda | A61H 33/063 |
| | | | 219/213 |
| 2002/0183814 A1 * | 12/2002 | Ono | A61F 7/0053 |
| | | | 607/100 |
| 2003/0156831 A1 * | 8/2003 | Schaeffer | A61N 5/06 |
| | | | 392/416 |
| 2004/0088028 A1 * | 5/2004 | Cameron | A61N 5/0614 |
| | | | 607/94 |
| 2004/0188415 A1 | 9/2004 | Lee | |
| 2004/0260364 A1 * | 12/2004 | Daffer | A61H 9/00 |
| | | | 607/81 |
| 2005/0050903 A1 | 3/2005 | Manteiga et al. | |
| 2005/0137656 A1 | 6/2005 | Malak | |
| 2005/0256554 A1 | 11/2005 | Malak | |
| 2007/0033069 A1 | 2/2007 | Rao et al. | |
| 2007/0050903 A1 | 3/2007 | Sappenfield et al. | |
| 2007/0110411 A1 | 5/2007 | Bergstein | |
| 2007/0206364 A1 | 9/2007 | Swei et al. | |
| 2007/0294818 A1 * | 12/2007 | Tei | A61H 33/06 |
| | | | 4/524 |
| 2008/0036383 A1 | 2/2008 | Lin | |
| 2009/0005839 A1 * | 1/2009 | Griffith | A61N 5/0614 |
| | | | 607/91 |
| 2009/0254153 A1 * | 10/2009 | Chang | A61H 33/06 |
| | | | 607/83 |
| 2010/0017953 A1 * | 1/2010 | O'Keeffe | A61H 33/06 |
| | | | 4/524 |
| 2012/0233765 A1 | 9/2012 | Altman et al. | |
| 2013/0097773 A1 | 4/2013 | Pinkus et al. | |
| 2015/0174003 A2 | 6/2015 | O'Keeffe et al. | |

* cited by examiner

PERSONAL SAUNA UNIT WITH INTEGRATED CHROMOTHERAPY LIGHTING

CROSS-REFERENCE TO RELATED APPLICATIONS

This application claims the benefit of U.S. Provisional Patent Application No. 62/298,768, filed Feb. 23, 2016, the disclosure of which is hereby incorporated herein in its entirety by reference.

BACKGROUND

Dry saunas are becoming increasingly popular as personal accessories in modern homes to deliver on-demand healthful dry heat therapy. These saunas are typically relatively small in size (housing from 1-6 individuals) and are constructed in a user's home as a semi-permanent, non-portable structure.

Personal saunas have also been developed that are intended for use by one person at a time and that are easily moveable for storage or transport to other locations. Such personal saunas are thus typically relatively compact and lightweight so as to reduce the overall footprint of the unit during both use and storage and to ease handling by the user.

Chromotherapy or light therapy has also become a popular addition to the personal health regimen of many people. Many psychological, physical emotional, and spiritual benefits are thought to stem from exposure to various colors or wavelengths of light in the visible spectrum. For example, red light may provide the user with the feeling of being energized, green light may aid healing processes, and blue light may aid mental relaxation among other potential benefits.

SUMMARY

Exemplary embodiments are defined by the claims below, not this summary. A high-level overview of various aspects thereof is provided here to introduce a selection of concepts that are further described in the Detailed-Description section below. This summary is not intended to identify key features or essential features of the claimed subject matter, nor is it intended to be used in isolation to determine the scope of the claimed subject matter. In brief, this disclosure describes a personal sauna unit with integrated chromotherapy lighting.

The personal sauna unit includes an upper and lower cabin each having a half-cylindrical form. The lower cabin is sized with a radius that is just smaller than that of the upper cabin such that the lower cabin can be moved relative to the upper cabin in a telescoping manner. The cabins are configured to overlie a user that is lying in a generally prone position on a surface with the head of the user extending beyond a terminal end of the upper cabin and the remainder of the user's body being enclosed between the cabins and the surface. A pad or mat may also be provided that can be placed on the surface beneath the user and the cabins.

A plurality of infrared heating elements are disposed in the walls of the upper and lower cabin to emit infrared radiation in one or more of near, mid, and far infrared bands and to direct the radiation toward the user's body. One or more heating elements may also be placed within the pad.

The upper cabin includes an integrated chromotherapy element disposed at or near the terminal end thereof. The light element is configured to direct light emitted therefrom toward the face of the user while the user is positioned in the sauna unit to simultaneously receive infrared- or heat- therapy and chromotherapy. The light element may be configured to emit light within one or more specific wavelengths or spectrums which may be selectable by the user.

The personal sauna unit includes a control unit through which the user may control the infrared heating elements independently or in groups. The control unit may also be employed to control the chromotherapy element and/or an additional control unit or remote control may be provided to allow the user to more easily control the light element during a sauna session.

DESCRIPTION OF THE DRAWINGS

Illustrative embodiments are described in detail below with reference to the attached drawing figures, and wherein.

DETAILED DESCRIPTION

Figure 1:
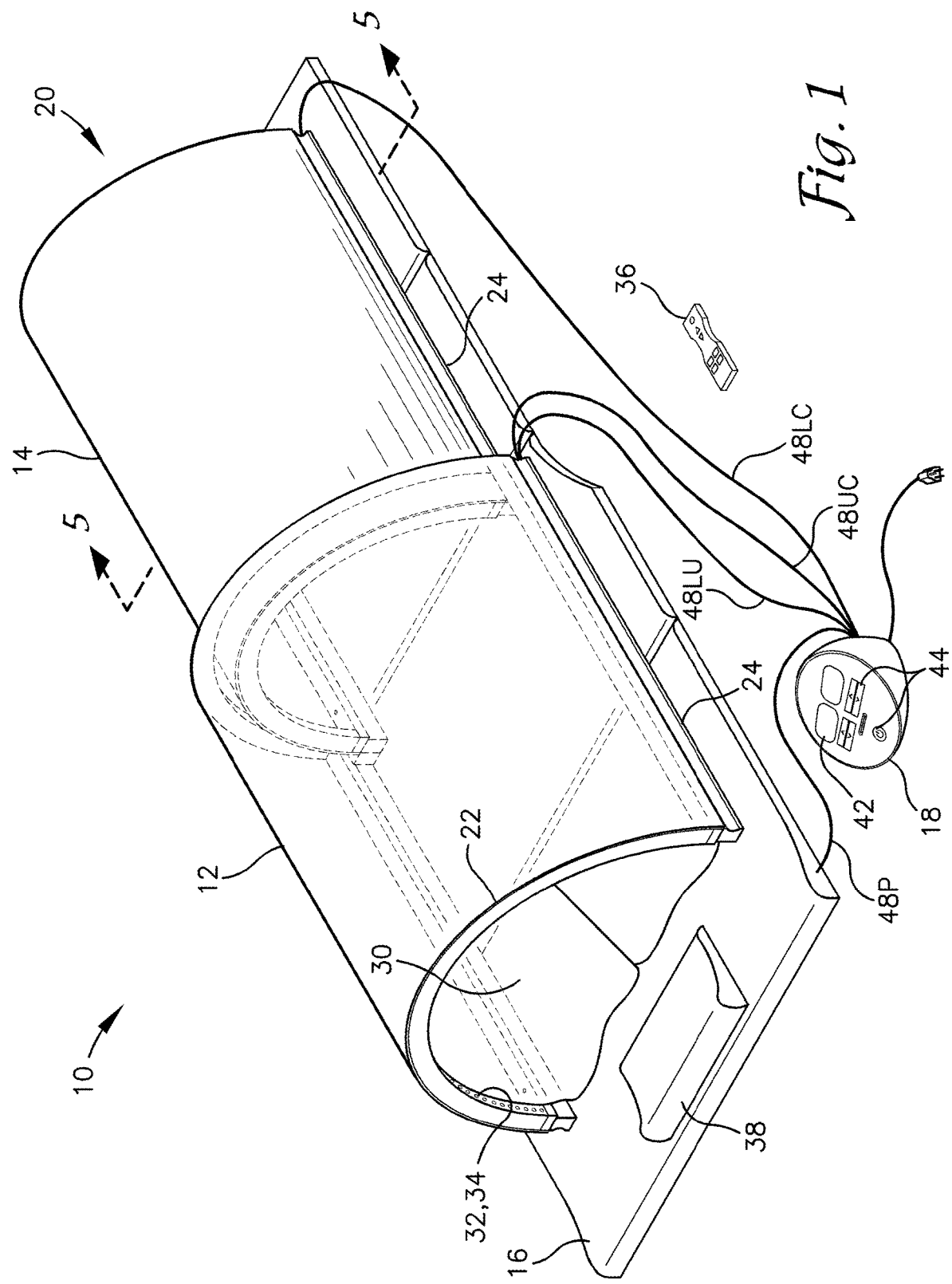
FIG. 1 is a perspective view of a personal sauna unit with integrated chromotherapy lighting depicted in accordance with an exemplary embodiment.
Figure 2:
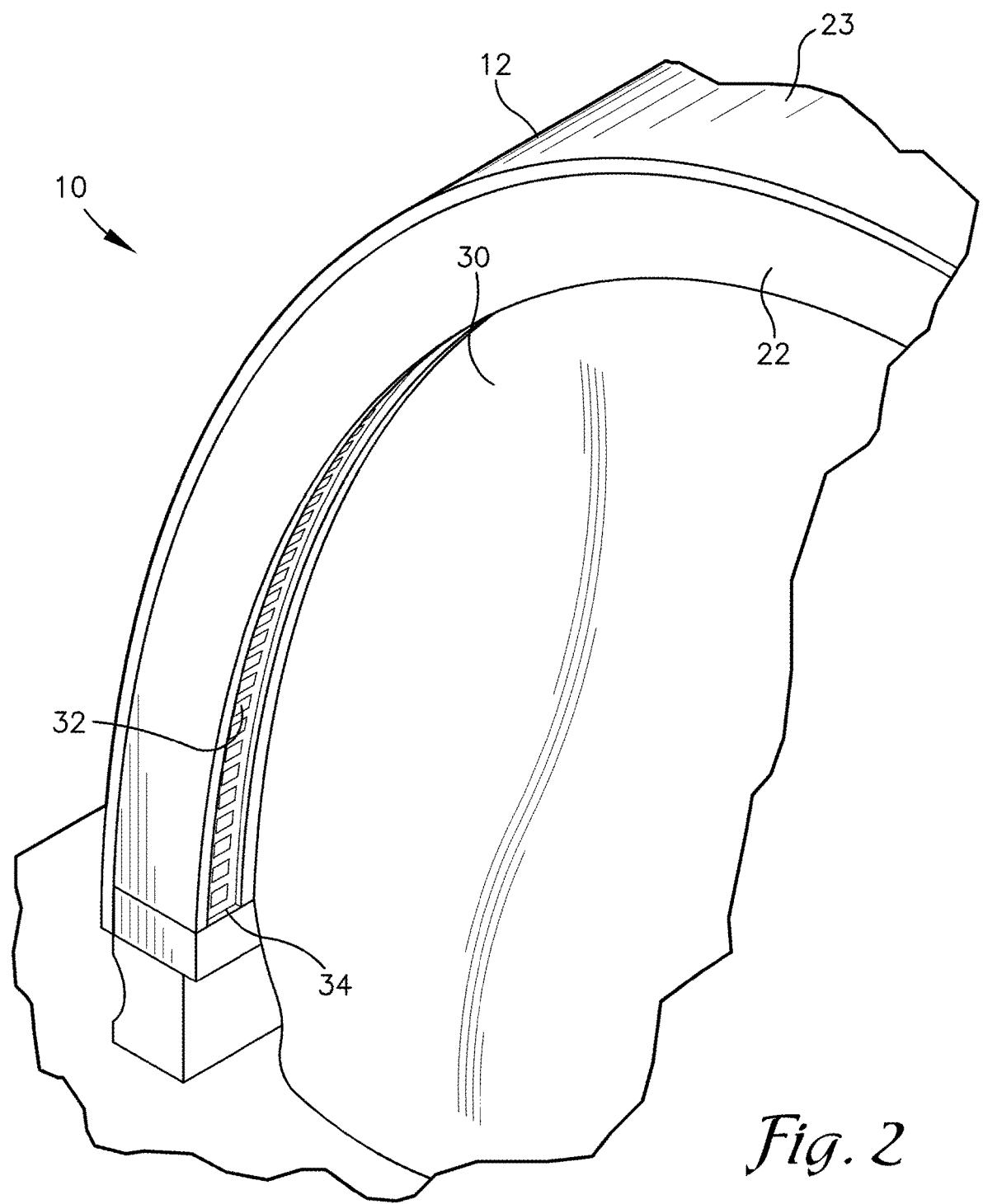
FIG. 2 is a partial enlarged perspective view of the integrated chromotherapy lighting of the personal sauna unit of FIG. 1.

The subject matter of select exemplary embodiments is described with specificity herein to meet statutory requirements. But the description itself is not intended to necessarily limit the scope of claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described. The terms "about" or "approximately" as used herein denote deviations from the exact value by +/−10%, preferably by +/−5% and/or deviations in the form of changes that are insignificant to the function.

With reference to FIGS. 1-6, a personal sauna unit 10 is described in accordance with an exemplary embodiment. The sauna unit 10 comprises an upper cabin 12, a lower cabin 14, a pad 16, and a control unit 18. The upper and lower cabins 12, 14 are each configured with a generally half-cylindrical form. The lower cabin 14 has a radial dimension that is slightly smaller than that of the upper cabin 12 such that the lower cabin 14 may be disposed at least partially within the upper cabin 12. The lower cabin 14 also includes an endwall 20 that encloses a distal end thereof. Although the upper and lower cabins 12, 14 are described herein with a half- or semi-cylindrical form, it is understood that other forms can be employed in embodiments of the invention without departing from the scope described herein.

The length of the upper and lower cabins 12, 14 is generally equal and when placed end-to-end is sufficient to enclose the body of a user from the user's shoulders down, e.g. the user's head and at least a portion of the user's neck extend beyond a terminal edge 22 of the upper cabin 12.

The upper and lower cabins 12, 14 may be telescopically moveable relative to one another to adjust the overall length of the sauna unit 10 and to allow the sauna unit 10 to be collapsed for storage and/or transportation. A rail or guide 24 may be provided along the longitudinal edges of the upper and lower cabins 12, 14 to guide and/or aid relative translational movement of the cabins 12, 14 along a floor surface. The guide 24 may slideably couple the upper and lower cabins 12, 14 along their longitudinal edges. Or the upper and lower cabins 12, 14 may be separate units that can be employed independently. For example, a user may use only one of the upper or lower cabins 12, 14 when a full body sauna treatment is not desired. The user might alternatively employ the upper cabin 12 in an upright, on-end position together with the lower cabin 14 in the lying down position such that the user can sit upright with her torso substantially within the upper cabin 12 and her legs extending beneath the lower cabin 14.

Figure 5:
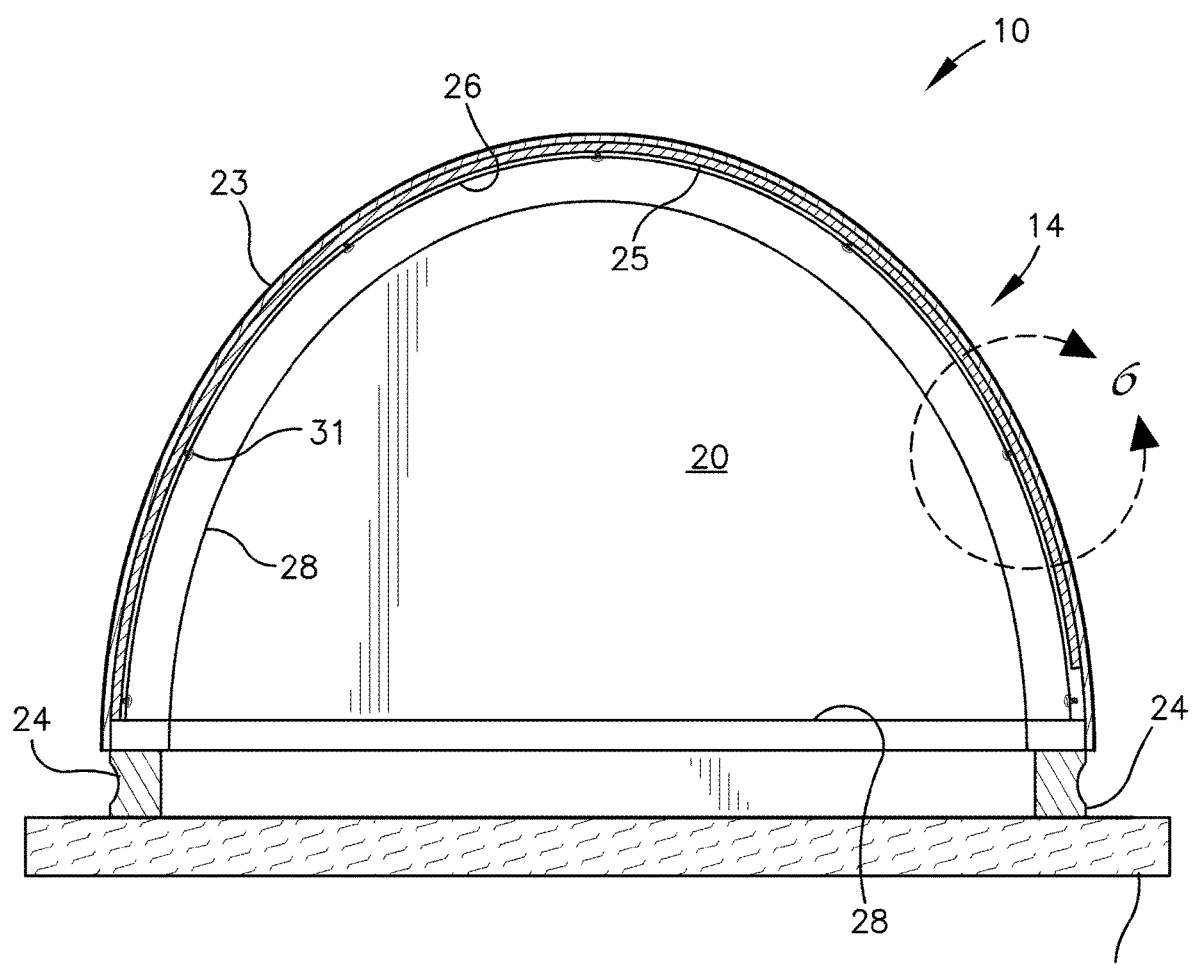
FIG. 5 is a cross-sectional view of the personal sauna unit of FIG. 1 taken along the line 5-5.

As shown in FIG. 5, the upper and lower cabins 12, 14 include a plurality of infrared heating elements 25 disposed within the walls thereof. One or more heating elements 25 may also be disposed within the endwall 20 of the lower cabin 14. The heating elements 25 preferably comprise infrared heating elements configured to emit radiation within one or more portions of the infrared spectrum. These include, for example, near infrared which is generally understood as the portion of the infrared spectrum having a wavelength between about 0.5 and about 1.5 micrometers (μm), mid infrared which generally comprises wavelengths between about 1.5 and about 7 μm, and far infrared which generally comprises wavelengths between about 7 and about 1000 μm although the boundaries of these portions of the spectrum may vary by application.

The heating elements 25 are preferably configured to produce no or very little electromagnetic field (EMF). In one embodiment, the heating elements 25 produce EMF that is less than about 3 milliGauss (mG), or more preferably less than about 0.03 mG. Sauna units incorporating infrared heating elements and technology that may be employed in embodiments of the invention are described in greater detail in U.S. Pat. No. 8,588,593 to Zach et al. and U.S. Pat. No. 8,676,044 to O'Keefe et al., both of which are incorporated herein in their entirety by reference.

In one embodiment, the heating elements 25 are flexible, planar heating elements like those described in U.S. Pat. No. 8,737,827 to Zach et al., the disclosure of which is hereby incorporated herein by reference. The flexibility and planar form of the heating elements 25 aids installation in the curved walls of the upper and lower cabins 12, 14. In another embodiment, the heating elements 25 may comprise or include more than one type of heating element including, for example, infrared LEDs, halogen bulbs, ceramic heating elements, and the like, which emit one or more of near-, mid-, and far-infrared radiation. As such, the user may be simultaneously provided with infrared radiation in one, two, or all three of the near-, mid-, and far-infrared spectrums.

Each of the heating elements 25 may be independently controllable or may be controlled as a group with one or more other heating elements 25. Independent control of the heating elements 25 may enable a user to tailor regions of the user's body that are targeted for application of the infrared radiation therapy.

Figure 6:
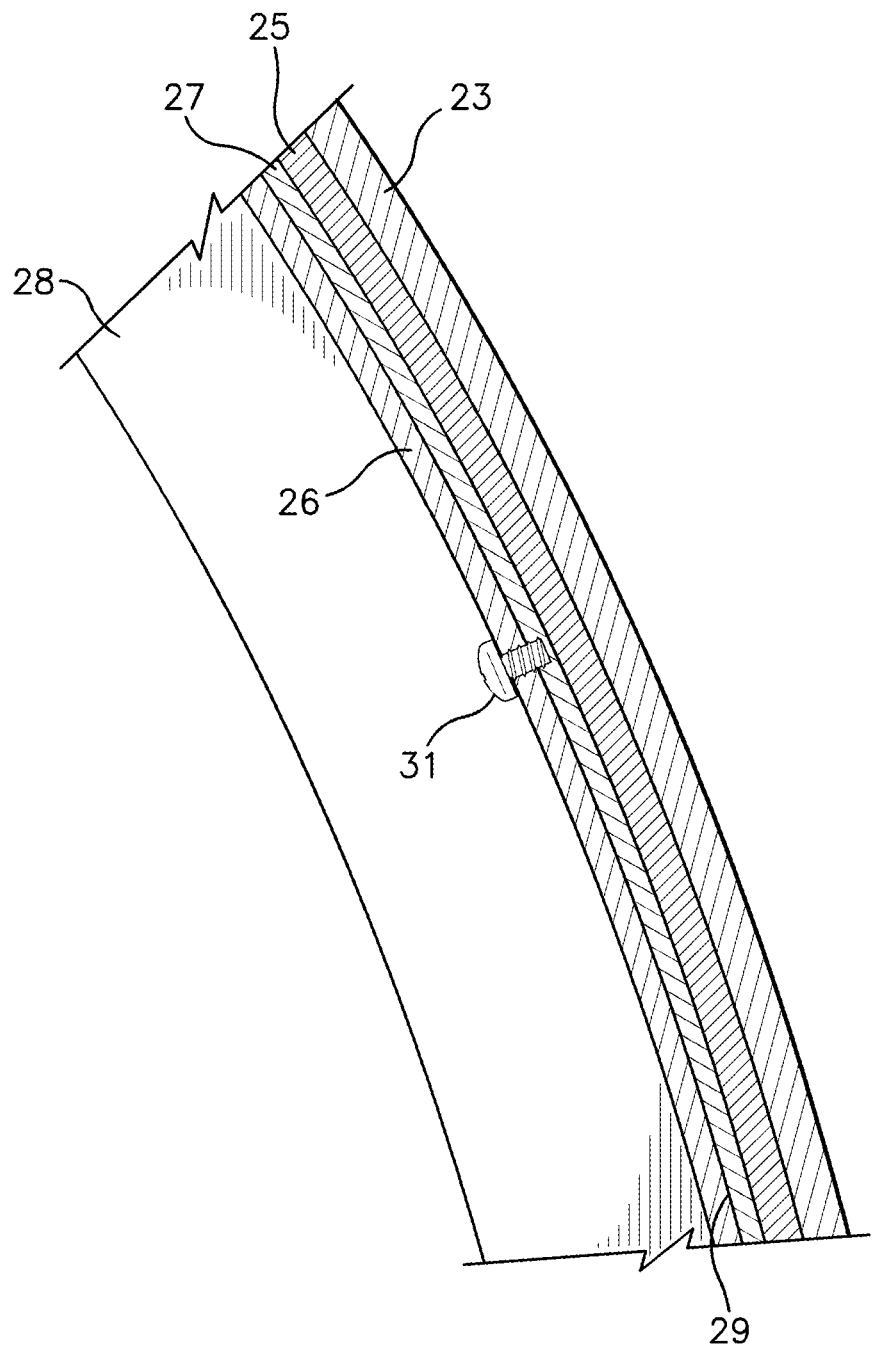
FIG. 6 is an enlarged view of a portion of the cross-sectional view of FIG. 5.

A liner 26 is disposed along an interior surface of the upper and the lower cabin 12, 14, as shown in FIGS. 5 and 6. The liner 26 may be at least partially comprised of a fabric formed from carbonized bamboo filament alone or in combination with other fibers, among other fabrics, materials, and textiles. An exterior covering 23 is provided on an exterior surface of the upper and lower cabins 12, 14 and may be comprised of materials that are similar or different from that of the liner 26.

Mounting ribs 27 are disposed alongside frame members 28 of the upper and lower cabins 12, 14 for installation of the liner 26 thereon. The mounting ribs 27 are disposed along opposing faces of the frame members 28 and in abutment therewith and follow the arcuate path of the frame members 28 along the wall of the respective upper or lower cabin 12, 14. In another embodiment, the mounting ribs 27 are integral with the frame members 28.

The mounting ribs 27 provide a mounting surface 29 to which the liner 26 may be coupled using for example, a plurality of fasteners 31, glues, adhesives, hook-and-loop fasteners, or the like. The mounting surface 29 is preferably even with or just interior to the interior most surface of the heating elements 25, however the mounting surface 29 may be positioned further toward the exterior of the upper or lower cabin 12, 14 than the surface of the heating elements 25. The liner 26 can thus be spaced radially inward and apart from the heating elements 25 or can be placed in contact with the surface of the heating elements 25. Spacing of the liner 26 away from the heating elements 25 may protect the user from direct contact with hot surfaces of the heating elements 25 during use of the sauna unit 10.

Such a configuration avoids a need to attach the liner 26 directly to the surface of heating elements using one or more glues or adhesives. The glues used when gluing directly to the heating elements decrease the effectiveness of the heating elements and may provide a source of noxious vapors or chemicals that may be given off during manufacturing or use of the sauna unit 10. And contact by the user with glued-on liners can result in the user being burned. Coupling of the liner 26 to the mounting ribs 27 and/or the frame 28 eliminates the use of glues and their effect on the operation, construction, and use of the sauna unit 10.

The upper cabin 12 includes a curtain 30 disposed near but spaced apart from the terminal edge 22 thereof. The curtain 30 comprises one or more sections of a flexible material that extend across the distal end of the upper cabin 12 to substantially enclose the opening formed thereby. In one embodiment, the curtain 30 is comprised of a fabric formed from carbonized bamboo filament alone or in combination with other natural and/or synthetic fibers. The curtain 30 may be configured to aid retention of heat produced by the heating elements 25 within the interior of the sauna unit 10. The curtain 30 also aids to enclose a gap between a user's body and the upper cabin 12 when the user is positioned in the sauna unit 10.

A chromotherapy light unit 32 is disposed between the curtain 30 and the terminal edge 22 of the upper cabin 12. The light unit 32 might alternatively be disposed in or coupled to the terminal edge 22. A recessed trough 34 is formed on an interior side of the upper cabin 12 between the curtain 30 and the terminal edge 22. The light unit 32 is disposed within the trough 34 and preferably extends along nearly the full perimeter of the upper cabin 12 but may extend along only one or more portions of the perimeter.

In one embodiment, the light unit 32 comprises a plurality of light emitting diodes (LEDs) that may be arranged or disposed on a tape-like strip, in a tubular enclosure, encased in a plastic or similar coating or potting material, or individually installed on the upper cabin 12, among a variety of other configurations. In another embodiment, the light unit 32 may be or include one or more wave guides, lenses, or the like to transfer, emit, focus, filter, or disperse light produced by the light unit 32 in a desired manner. Similarly, the light may be produced from non-LED sources, such as incandescent bulbs, halogen bulbs, lasers, or fluorescent bulbs, among other lighting technologies. LED's and fluorescent bulbs are preferred in many applications because they generate a limited amount of additional heat, are generally low-power, and produce very little or no EMF.

The light unit 32 is configured to emit light in the visible spectrum. The light unit 32 is preferably configured to selectively produce light within one of a plurality of predetermined colors or wavelength ranges and to enable selection and changing of the produced color by the user, e.g. the user can select and change between red, orange, yellow, green, blue, or violet. Or multiple colors might be selected and emitted simultaneously. In another embodiment, the light unit 32 is configured to produce only a single predetermined color of light. The color and intensity may also be selectively emitted and varied based on one or more preprogrammed sequences. In one embodiment, the light unit 32 is configured to emit infrared radiation in addition to light within the visible spectrum. For example, LEDs configured to emit in the near and/or mid-infrared spectrums can be integrated in the light unit 32 or provided alongside the light unit 32.

The light unit 32 is positioned to direct the light produced thereby toward the face and or eyes of a user positioned within the sauna unit 10 with her head extending from the upper cabin 12 and adjacent to the light unit 32. The user's face and eyes can thus be illuminated with a desired color of light to provide chromotherapy thereto. The chromotherapy may be provided during or simultaneously with a sauna session or independent of the operation of the heating elements 25.

Figure 3:
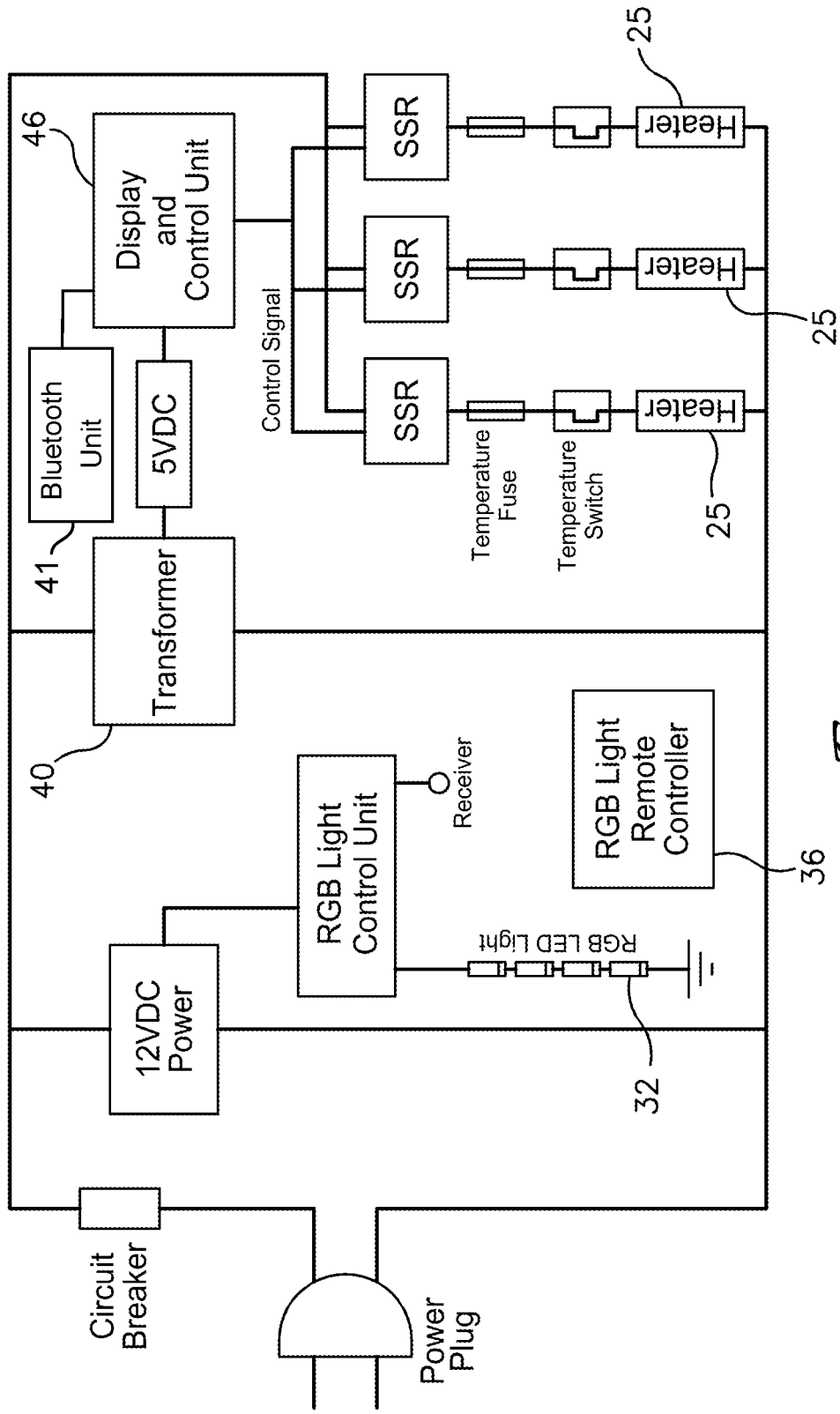
FIG. 3 is a block diagram of a circuit configuration for use in a personal sauna unit with integrated chromotherapy depicted in accordance with an exemplary embodiment.
Figure 4:
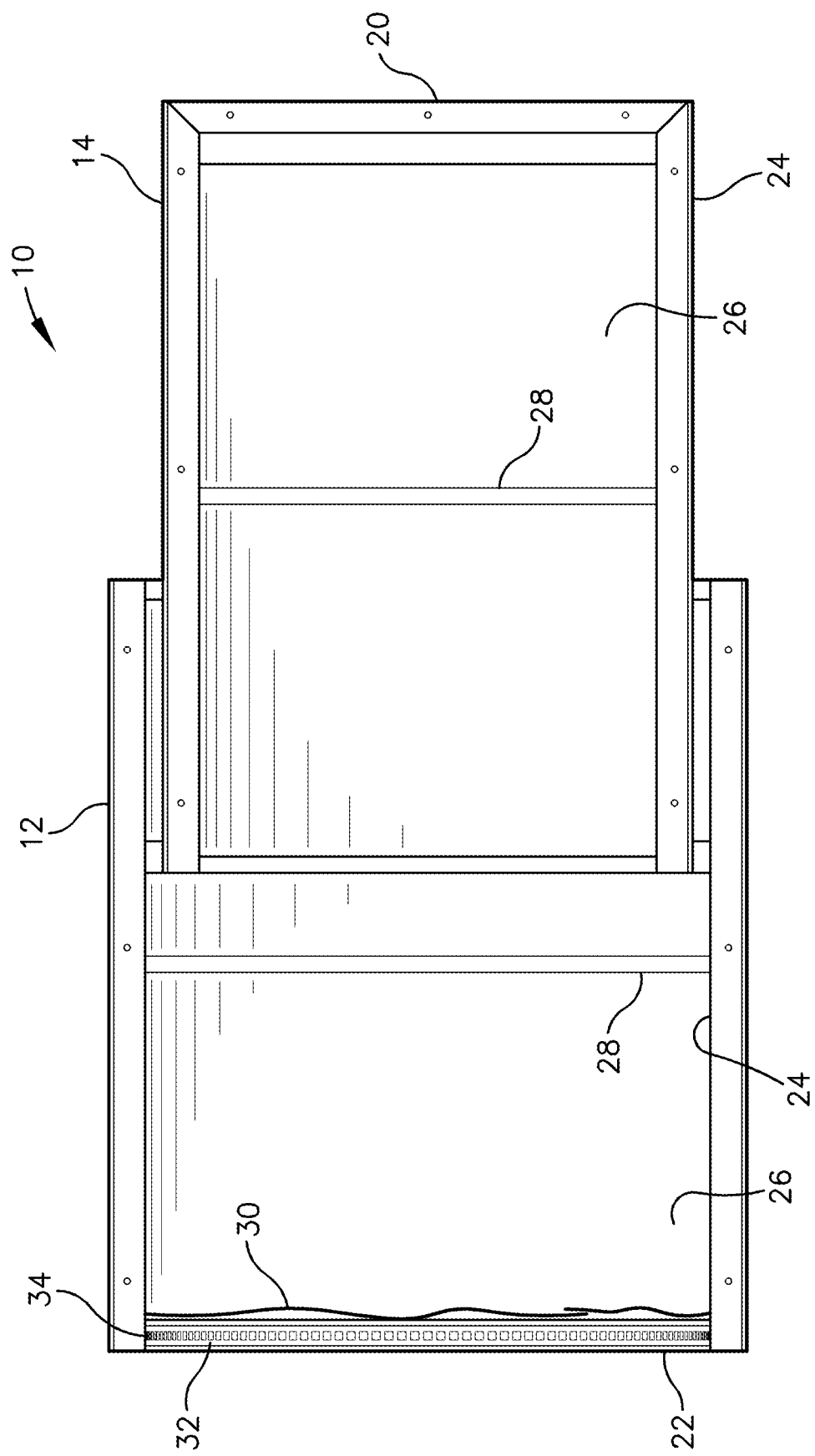
FIG. 4 is a bottom plan view of a cabin of the personal sauna unit of FIG. 1 showing sections of the cabin in a partially collapsed state depicted in accordance with an exemplary embodiment.

As depicted in FIGS. 1 and 3, a wireless or wired remote control unit 36 may be provided to enable the user to turn the light unit 32 on/off and/or to select a desired color of light emitted thereby. The remote control 36 can be held in the hand of the user while inside the sauna unit 10, thus eliminating any need for the user to exit the sauna unit 10 to operate the light unit 32. The remote control 36 may include tactile features that aid the user in identifying buttons and their functions by touch.

The pad 16 comprises a generally planar component formed from a cushioning material, such as a foam, rubber, inflatable bladder(s), or the like. Preferably the pad 16 comprises a memory foam material. The pad 16 may include one or more outer layer materials that enclose the cushioning material, such as a material constructed at least partially from carbonized bamboo fibers. The outer layer materials may provide antimicrobial properties and resistance to sweat or water, among other characteristics.

The pad 16 is divided into a plurality of sections that are pivotably joined together to assist folding of the pad 16 for storage or transport. In another embodiment, the pad 16 is a single continuous section that can be rolled upon itself for storage/transport. The pad has a length sufficient to extend the full length of the upper and lower cabins 12, 14 placed end-to-end with the addition of a sufficient length to accommodate the user's head extending from the upper cabin 12. The width of the pad 16 can extend beyond the outer perimeter of the upper and lower cabins 12, 14 or can be sized to fit within the perimeter.

A plurality of the heating elements 25 are disposed within the body of the pad 16 to emit infrared radiation toward the user lying thereon. The pad 16 may include a pillow 38 that is integrated with one of the sections thereof or that is included separately with the pad 16. The pillow 38, if separate from the pad 16, may be removably coupled to the pad 16, such as by hook-and-loop fasteners, buttons, snaps, or the like.

The control unit 18 is electrically coupled to the upper cabin 12, the lower cabin 14, the pad 16, and the chromotherapy light unit 32 to provide power thereto and to control operations thereof. The control unit 18 receives power from an electrical coupling with a local power grid and distributes the power to each of the components of the sauna unit 10.

The power grid is typically an alternating current (AC) power source. Referring to FIG. 3, the control unit 18 includes one or more transformers 40 and other components useable to transform AC to direct current (DC) and to provide voltages useable by the heating elements 25 and the light unit 32. Conversion from AC to DC also aids to reduce or eliminate electromagnetic fields produced by the heating elements 25. Such AC to DC conversions take place within the control unit 18 and/or outside and separated from the upper and lower cabins 12, 14 so as to further eliminate or reduce potential exposure of the user to EMF.

A wireless communications unit, such as a BLUETOOTH unit 41 may be included in the control unit 18. The BLUETOOTH unit 41 may enable wireless operation/control of the sauna unit 10 (including the heating elements 25 and the light unit 32, among other functions) from a computing device such as a tablet computer, mobile device, smartphone, laptop computer, desktop computer, or the like. The BLUETOOTH unit 41 may employ the wireless communication standards managed by the Bluetooth Special Interest Group, and/or may utilize other wireless communication standards, such as WiFi based on IEEE 802.11 standards, among others.

A clip, clamp, or other mounting device (not shown) may also be provided on the sauna unit 10 for removeably mounting the computing device on the sauna unit 10 for use by the user during a sauna session. For example, a tablet computer may be coupled to the sauna unit 10 along the terminal edge 22 of the upper cabin 12 and held in view of the user such that the user can view video images and/or hear audio output from the tablet computer during the sauna session. The output from the computing device may provide entertainment content to the user and/or information associated with the sauna session or the operation of the sauna unit 10.

The control unit 18 includes a display 42 and one or more input components 44, such as buttons, switches, dials, or the like as well as one or more logic units 46 that are configured to operate the heating elements 25 and the light unit 32 in accordance with inputs provided by the user. The control unit 18 may include a plurality of cords 48 extending therefrom that can be electrically coupled to each of the upper cabin 12 (cord 48UC), the lower cabin 14 (cord 48LC), the pad 16 (cord 48P), and the light unit 32 (cord 48LU) to provide electrical communication therebetween. Alternatively, the cords 48 may extend from the upper and lower cabins 12, 14, the pad 16, and the light unit 32 and couple to ports provided on the control unit 18. The cord 48LU for the light unit 32 may be integrated into the upper cabin 12 and/or with the cord 48UC for the upper cabin 12 to reduce the number of cords 48 extending from the upper unit 12 and/or to provide a more aesthetically pleasing appearance.

In operation, a user deploys the pad 16 on a floor surface. The lower cabin 14 and upper cabin 12 may then be placed on the pad 16 with the upper cabin 12 at least partially overlapping the lower cabin 14. The cords 48 are coupled between the pad 16, upper cabin 12, lower cabin 14, and the light unit 32 and the control unit 18 and the control unit 18 is coupled to a power grid to receive electrical power therefrom.

The user selects a desired heating profile, e.g. temperature, duration, etc. using the input components 44 and displays 42 provided on the control unit 18. One or more preprogrammed heating cycles might be provided by the control unit 18 and may be selectable by the user. For example, heating cycles might be preprogrammed into the control unit 18 by the user or during manufacturing. The control unit 18 might also be configured to provide a dynamic sauna experience in which biological data is collected from the user and employed to select or adjust heating cycles. For example, the user might wear a heart rate monitor that allows the control unit 18 to adjust a heating cycle based on the user's heart rate.

The user may enter the sauna unit 10 by sitting on the pad 16 and inserting her legs into the lower cabin 14. The user might next lie down on the pad 16 and manually telescopically extend the upper cabin 12 from its position overlapping the lower cabin 14 toward her head and over her torso. As a result, the user is enclosed between the pad 16 and the upper and lower cabins 12, 14 with her head and neck extending through the curtain 30 and outside of the upper cabin 12. The user can thus remain enclosed within the sauna unit 10 for the duration of her desired sauna treatment.

The user may also initiate a chromotherapy treatment simultaneously with her sauna treatment or without energizing the heating elements 25. The chromotherapy light unit 32 may be initiated and controlled via the control unit 18 and/or via a remote control 36 which the user can keep in-hand while within the sauna unit 10. The user is preferably able to select a desired light color or colors to be emitted by the light unit 32. The user may also be provided with the option to select one or more illumination sequences which may include various color changing sequences, light pulsing sequences, and/or light dimming sequences or options, among other lighting characteristics.

While within the sauna unit 10 as described above, the user's head is just outside the upper cabin 12 and near the terminal edge 22 thereof. The light unit 32 is thus positioned to illuminate the user's face to provide the chromotherapy treatment. The user may hold the remote control 36 in a hand while inside the sauna unit 10 and can thus control the light unit 32 without need to move her body (other than for her hand) and without need to exit the upper or lower cabins 12, 14 during the sauna session.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Identification of structures as being configured to perform a particular function in this disclosure and in the claims below is intended to be inclusive of structures and arrangements or designs thereof that are within the scope of this disclosure and readily identifiable by one of skill in the art and that can perform the particular function in a similar way. Certain features and sub-combinations are of utility and may be employed without reference to other features and sub-combinations and are contemplated within the scope of the claims.

What is claimed is:

1. A personal sauna unit comprising:
   a cabin that is disposable on a surface to define an interior space between a wall of the cabin and the surface in which a single user can be positioned with a head and face of the user extending at least partially from a terminal end of the cabin;
   a heating element disposed in the wall of the cabin and directed toward the interior space to provide infrared radiation to the user positioned within the cabin;
   a chromotherapy unit disposed at the terminal end of the cabin and directed toward the face of the user when a body of the user is positioned within the cabin with the head and face of the user extending at least partially from the terminal end of the cabin, the chromotherapy unit emitting visible light at a wavelength corresponding to a selected color of visible light; and
   a curtain disposed near the terminal end of the cabin and separating the chromotherapy unit from the interior space of the cabin.

2. The personal sauna unit of claim 1, further comprising:
   a control unit electrically coupled to the heating unit, the chromotherapy unit, and a power supply, the control unit including an AC to DC transformer that converts a supply of AC power from the power supply to DC power, provision of the DC power to the heating unit and the chromotherapy unit being controlled by the control unit.

3. The personal sauna unit of claim 2, wherein a magnetic field produced within the cabin is less than 3 milliGauss.

4. The personal sauna unit of claim 1, wherein the chromotherapy unit is disposed in a trough formed in the wall of the cabin at the terminal end of the cabin.

5. The personal sauna unit of claim 1, wherein the chromotherapy unit comprises a plurality of LEDs.

6. The personal sauna unit of claim 1, wherein the chromotherapy unit includes an infrared emitter configured to emit infrared radiation in one or more of a near-, mid-, and far-infrared spectrum.

7. The personal sauna unit of claim 6, wherein the infrared emitter comprises an infrared LED.

8. The personal sauna unit of claim 1, wherein the heating element provides infrared radiation in one or more of a near-, mid-, and far-infrared spectrum.

9. The personal sauna unit of claim 8, wherein the heating element comprises at least two infrared emitting elements and provides infrared radiation in at least two of the near-, mid-, and far-infrared spectrums.

10. The personal sauna unit of claim 1, wherein the heating element comprises a planar heating element and further comprising:
    a fabric liner disposed interior to the heating element and spaced inwardly apart from the heating element.

11. The personal sauna unit of claim 10, further comprising:
    a frame member forming a support structure of the cabin and having a frame-member face directed radially inward toward the interior space of the cabin; and
    a mounting rib positioned alongside the frame member and providing a mounting face on which the liner is disposed, the mounting face being positioned radially between and spaced apart from the frame-member face and an innermost face of the heating element.

12. A personal sauna unit comprising:
a cabin that is disposable on a surface to define an interior space between an interior wall of the cabin and the surface, the cabin including an upper portion and a lower portion that are telescopically movable relative to one another, the cabin being sized to receive a single user within the interior space with a head and face of the user extending at least partially beyond a terminal end of the upper portion of the cabin;
a heating element disposed in the wall of the cabin and directed toward the space to provide infrared radiation to the user positioned within the cabin;
a curtain disposed near the terminal end of the upper cabin, the curtain substantially enclosing the interior space; and
a chromotherapy unit disposed at the terminal end of the upper portion of the cabin and directed toward the face of the user when a body of the user is positioned within the cabin with the head and face of the user extending at least partially from the terminal end of the cabin, the chromotherapy unit emitting visible light at a wavelength corresponding to a selected color of visible light, and the chromotherapy unit being separated from the interior space of the cabin by the curtain.

13. The personal sauna unit of claim 12, further comprising:
a wireless remote control configured to be held in hand by the user when positioned in the cabin and useable to control operation of the chromotherapy unit.

14. The personal sauna unit of claim 13, wherein the wireless remote control employs one or more of BLUETOOTH and WiFi wireless communication standards to communicate with a control unit that is configured to control operation of the chromotherapy unit.

15. The personal sauna unit of claim 12, wherein the heating element provides infrared radiation to the user in at least two of near-, mid-, and far-infrared spectrums.

16. The personal sauna unit of claim 12, further comprising:
a mounting rib extending transversely along the wall of at least one of the upper portion and the lower portion of the cabin, the mounting rib providing a mounting face that is positioned further inward toward the interior space of the cabin that an innermost face of the heating element; and
a fabric liner forming an interior face of at least one of the upper portion and the lower portion of the cabin, the liner being disposed on the mounting face of the mounting rib and spaced inwardly apart from the innermost face of the heating element.

17. A personal sauna unit comprising:
a cabin that is disposable on a surface, the cabin and surface defining an interior space that is sized to receive a body of a user with a head and face of the user extending at least partially beyond a terminal end of the cabin;
a heating element disposed in a wall of the cabin and directed toward the interior space to provide infrared radiation to the user positioned within the cabin;
a fabric liner forming at least a portion of an interior face of the wall of the cabin, the liner being positioned inwardly of and spaced apart from an innermost face of the heating element;
a curtain disposed near the terminal end of the cabin, the curtain substantially enclosing the interior space;
a chromotherapy unit disposed at the terminal end of the cabin and directed toward the face of the user when the body of the user is positioned within the cabin, the chromotherapy unit emitting visible light at a wavelength corresponding to a selected color of visible light, and the chromotherapy unit being separated from the interior space of the cabin by the curtain.

18. The personal sauna unit of claim 17, wherein the wall of the cabin includes a recessed trough formed in the interior face and at the terminal end, and wherein the chromotherapy unit is disposed in the trough.

19. The personal sauna unit of claim 17, wherein the chromotherapy unit includes an infrared emitting element configured to emit infrared radiation toward the face of the user with a wavelength in at least one of a near-, mid-, and far-infrared spectrum.

* * * * *